US010449288B2

(12) United States Patent
Tsang et al.

(10) Patent No.: US 10,449,288 B2
(45) Date of Patent: Oct. 22, 2019

(54) IRRIGATION AND ASPIRATION DEVICE

(71) Applicant: myKare.net, LLC, Raleigh, NC (US)

(72) Inventors: Man-Yee Karen Tsang, Raleigh, NC (US); Mark Donald Piehl, Chapel Hill, NC (US); Joseph Charles Ferrante, III, Chapel Hill, NC (US)

(73) Assignee: myKare.net, LLC, Raleigh, NC (US)

( * ) Notice: Subject to any disclaimer, the term of this patent is extended or adjusted under 35 U.S.C. 154(b) by 301 days.

(21) Appl. No.: 15/282,185

(22) Filed: Sep. 30, 2016

(65) Prior Publication Data
US 2018/0093034 A1 Apr. 5, 2018

(51) Int. Cl.
*A61M 3/02* (2006.01)
*A61M 1/00* (2006.01)
*A61M 39/22* (2006.01)

(52) U.S. Cl.
CPC ........ *A61M 3/0262* (2013.01); *A61M 1/0003* (2013.01); *A61M 1/0058* (2013.01); *A61M 3/0283* (2013.01); *A61M 39/22* (2013.01); *A61M 2205/8275* (2013.01); *A61M 2210/0618* (2013.01)

(58) Field of Classification Search
CPC .............. A61M 3/0262; A61M 1/0003; A61M 1/0058; A61M 3/0283; A61M 39/22; A61M 2205/8275; A61M 2210/0618
See application file for complete search history.

(56) References Cited

U.S. PATENT DOCUMENTS

| 4,596,343 | A | * | 6/1986 | Ford, Jr. | ................. | A45D 27/10 |
| | | | | | | 222/190 |
| 4,801,292 | A | * | 1/1989 | Watson | ............... | A61M 3/0229 |
| | | | | | | 604/185 |
| 6,517,511 | B2 | | 2/2003 | Yao | | |
| 7,981,077 | B2 | | 7/2011 | Hoke et al. | | |
| 8,048,023 | B2 | | 11/2011 | Hoke et al. | | |
| 2009/0281482 | A1 | | 11/2009 | Baker et al. | | |
| 2014/0121592 | A1 | * | 5/2014 | Rubin | ................. | A61M 3/0233 |
| | | | | | | 604/30 |

* cited by examiner

*Primary Examiner* — Lauren P Farrar
(74) *Attorney, Agent, or Firm* — Dicke, Billig & Czaja, PLLC

(57) ABSTRACT

An irrigation and aspiration device includes a drive assembly, an evacuation chamber, and a delivery apparatus. The delivery apparatus includes an evacuation tube configured to hold an irrigation solution and a vacuum tube that is in fluid communication with the evacuation chamber. The drive assembly is configured to store a restoration energy within the evacuation chamber and force the irrigation solution out of the evacuation tube in response to an applied force. The device is configured to use the restoration energy to draw an aspiration fluid into the vacuum tube.

18 Claims, 11 Drawing Sheets

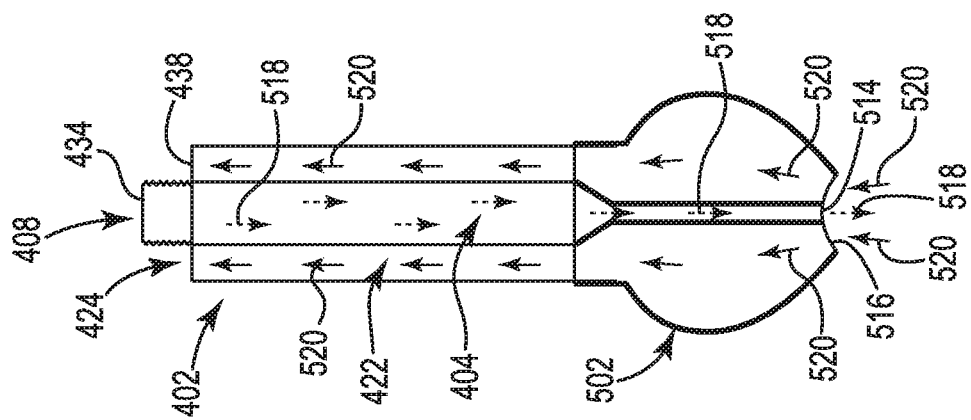
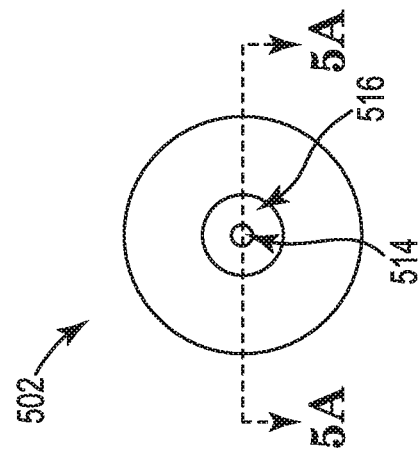
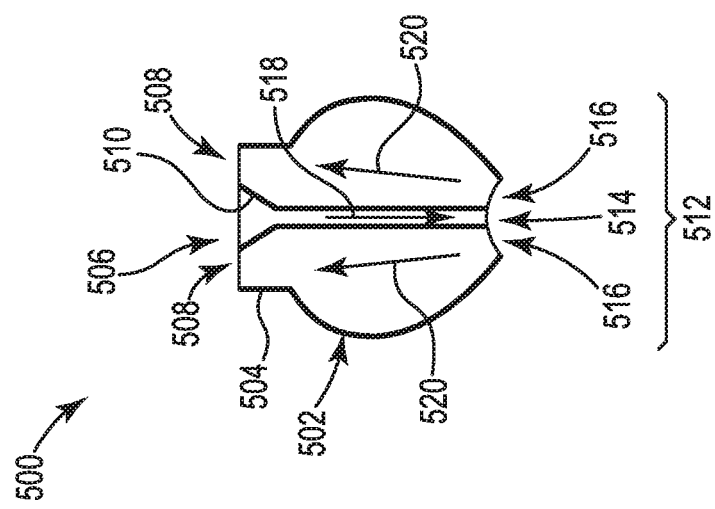
Fig. 5C
Fig. 5B
Fig. 5A

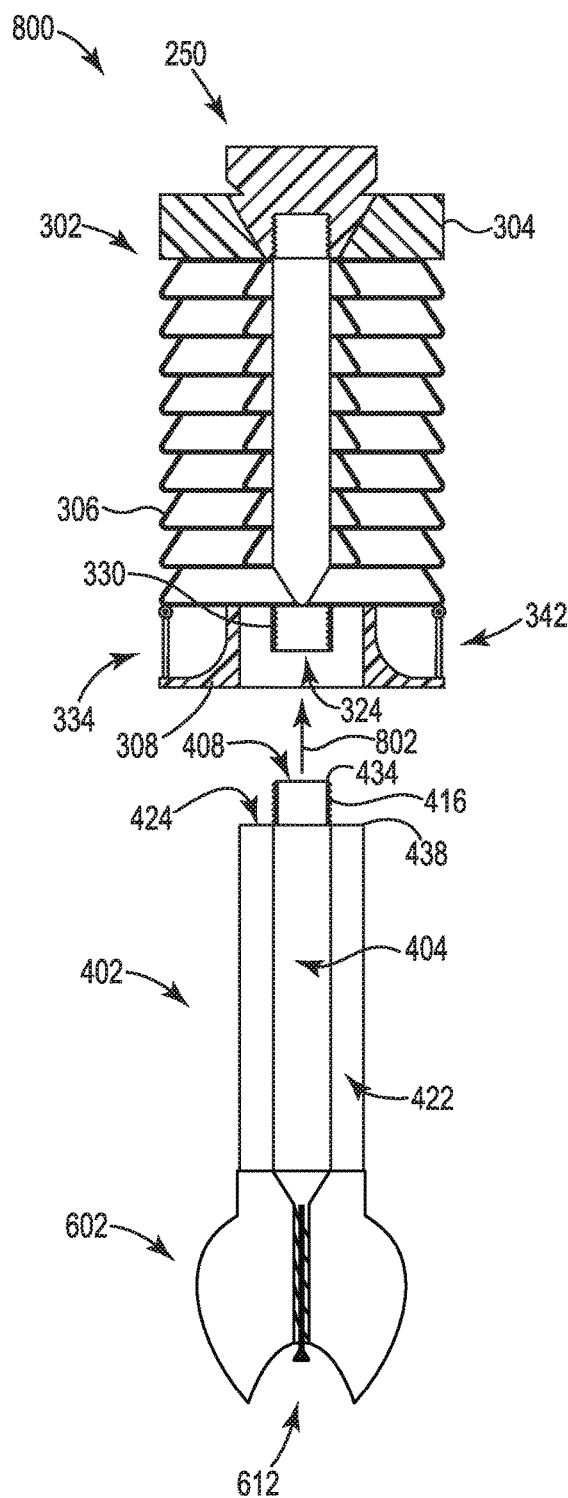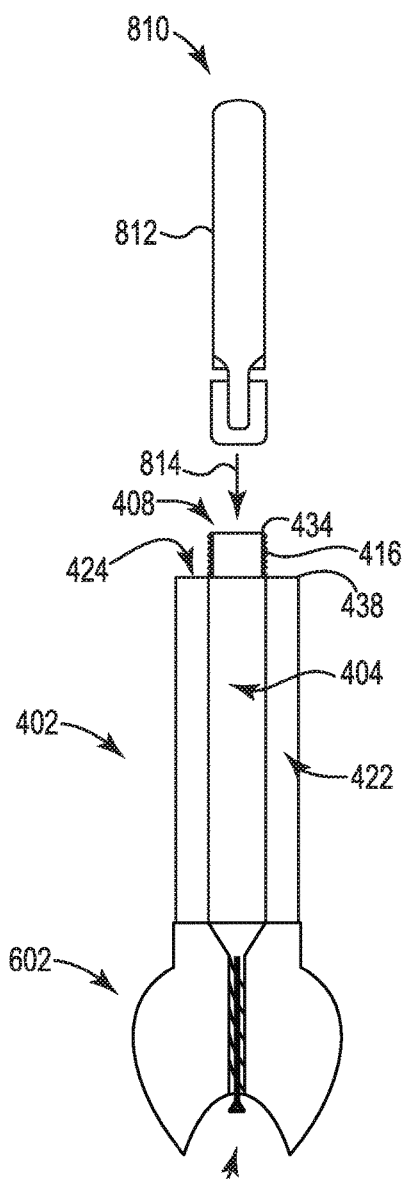
Fig. 8A
Fig. 8B

IRRIGATION AND ASPIRATION DEVICE

FIELD OF TECHNOLOGY

The present application relates to an irrigation and aspiration device, in particular, an irrigation and aspiration device that stores a restoration energy while forcing out an irrigation solution and uses the restoration energy to draw an aspiration fluid.

BACKGROUND

Nasal and sinus congestion is a common problem for both infants and adults. Viral illnesses as well as allergies can cause a multitude of symptoms that result in congestion and nasal cavity blockage and difficulty in breathing. With newborn babies, nasal and sinus congestion due to nasal cavity blockage can be life threatening and must be dealt with in a fast, gentle and effective manner.

There are a number of nasally administered approaches that have been used with newborn babies. One approach that has been used is a bulb suction syringe. Bulb suction syringes have an insertion tip which can be inserted into a nasal cavity to suction in mucous to the bulb. The insertion tips for these devices however tend to be narrow and can damage an infant's nasal cavity. These tips also provide a seal which is inadequate for effective nasal lavage.

It has been shown that a combination of saline irrigation and nasal suctioning can be effective in removing mucosal blockage. There are a number of solutions available that can provide both these functions. These solutions however tend to be complex, expensive and require batteries to operate. They also lack the antibacterial properties and the simple, single-handed operation desired for a delivery room environment.

For these and other reasons, there is a need for the present invention.

SUMMARY

According to an embodiment of an irrigation and aspiration device, the device includes a drive assembly, an evacuation chamber, and a delivery apparatus. The delivery apparatus includes an evacuation tube configured to hold an irrigation solution and a vacuum tube that is in fluid communication with the evacuation chamber. The drive assembly is configured to store a restoration energy within the evacuation chamber and force the irrigation solution out of the evacuation tube in response to an applied force. The device is configured to use the restoration energy to draw an aspiration fluid into the vacuum tube.

According to an embodiment of an irrigation and aspiration device, the device includes a drive assembly, an evacuation chamber and a delivery apparatus. The evacuation chamber includes an input port, an evacuation port and a vacuum port. The drive assembly is in axial alignment with the input port and the evacuation port, and the input port and evacuation port are separated by a distance. The drive assembly is configured to be releasably retained within the input port and movably engaged within the evacuation port. The delivery apparatus includes an evacuation tube configured to retain an irrigation fluid and includes a vacuum tube. A proximal end of the evacuation tube is attached to and in a fluid sealing relationship with the evacuation port and a proximal end of the vacuum tube is attached to and in a fluid sealing relationship with the vacuum port. The drive assembly is configured to be moved in cooperation with the evacuation chamber to reduce the distance between the input port and the evacuation port to store a restoration energy and push a distal end of the drive assembly into the proximal end of the evacuation tube to force the irrigation fluid out of a distal end of the evacuation tube. The device is configured to release the restoration energy to increase the distance between the input port and the evacuation port to create a negative pressure within the evacuation chamber that operates to draw in the aspiration fluid from a distal end of the vacuum tube.

According to an embodiment of a method of irrigating and aspirating a nasal cavity, the method includes providing a device that includes a drive assembly, an evacuation chamber and a delivery apparatus. The evacuation chamber includes an input port, an evacuation port and a vacuum port. The delivery apparatus includes a vacuum tube and an evacuation tube. The evacuation tube is configured to retain an irrigation fluid. The method includes applying a force to move the drive assembly in cooperation with the evacuation chamber to reduce a volume of the evacuation chamber to store a restoration energy and to force the irrigation fluid out of the evacuation tube. The method includes using the restoration energy to increase the volume of the evacuation chamber to draw in an aspiration fluid into the vacuum tube.

Those skilled in the art will recognize additional features and advantages upon reading the following detailed description, and upon viewing the accompanying drawings.

BRIEF DESCRIPTION OF THE DRAWINGS

The elements of the drawings are not necessarily to scale relative to each other. Like reference numerals designate corresponding similar parts. The features of the various illustrated embodiments can be combined unless they exclude each other. Embodiments are depicted in the drawings and are detailed in the description which follows.

FIGS. 5A-5C illustrate cross-sectional, bottom and assembled views of an embodiment of a nozzle.

FIGS. 8A and 8B illustrate a cross-sectional view of an embodiment of insertion of an irrigation fluid packet into a delivery apparatus.

DETAILED DESCRIPTION

Figure 1:
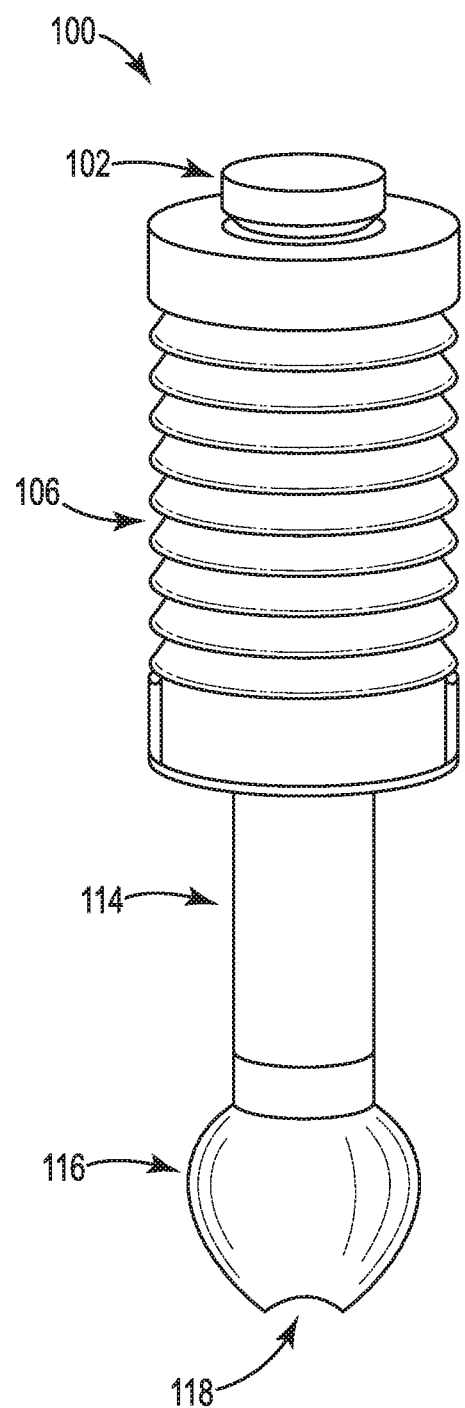
FIG. 1 illustrates a perspective view of an embodiment of an irrigation and aspiration device.

FIG. 1 illustrates a perspective view of an embodiment of an irrigation and aspiration device at 100. The device 100 includes a drive assembly 102, an evacuation chamber 106 and a delivery apparatus 114. Delivery apparatus 114 includes a nozzle 116. In other embodiments, delivery apparatus 114 does not include a nozzle 116. In the illustrated embodiment, delivery apparatus 114 is configured to retain an irrigation solution. In one embodiment, the irrigation solution is a saline solution. In other embodiments, the irrigation solution can be other suitable solutions.

In the illustrated embodiment, application of a force to drive assembly 102 causes a restoration energy to be stored within evacuation chamber 106 while forcing the irrigation solution out of delivery apparatus 114 and through port 118 of nozzle 116. Device 100 uses the restoration energy stored within evacuation chamber 106 to draw in an aspiration fluid through port 118. In the illustrated embodiment, the irrigation solution is forced through port 118 prior to drawing in the aspiration fluid. In other embodiments, the acts of providing the irrigation solution and drawing in the aspiration fluid can overlap or can occur simultaneously.

In the illustrated embodiment, a port 118 at an end of nozzle 116 is used to dispense an irrigation solution and to draw in or suction in an aspiration fluid. In the illustrated embodiments, device 100 is used for irrigation and drainage of a nasal cavity. Device 100 is adapted to lubricate a nasal cavity before cleaning the cavity by drawing in the aspiration fluid. This action quickly and effectively clears the nasal cavity and provides for unrestricted breathing.

Figure 2C:
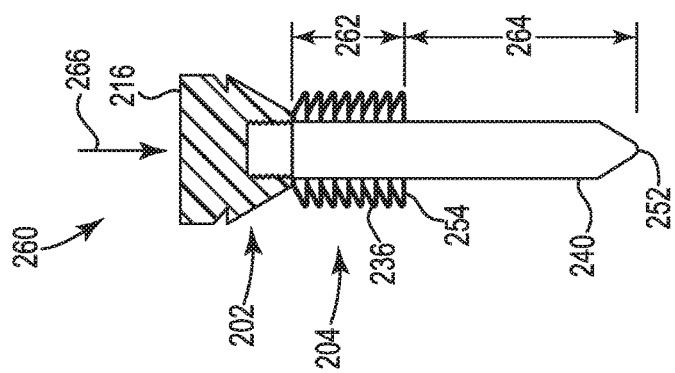
FIGS. 2A-2C illustrate disassembled and assembled cross-sectional views of an embodiment of a drive assembly.
Figure 2B:
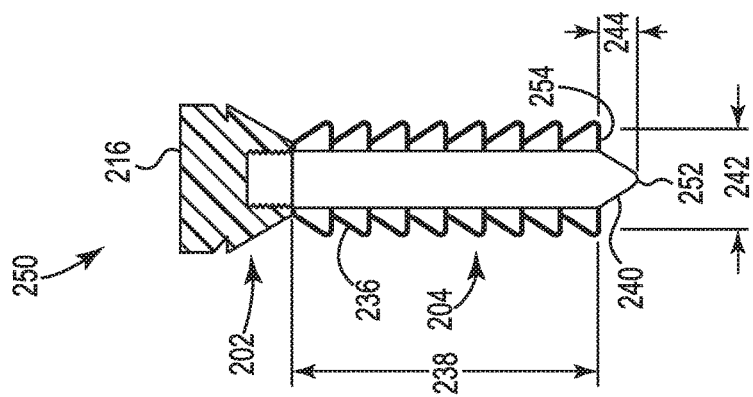
Figure 2A:
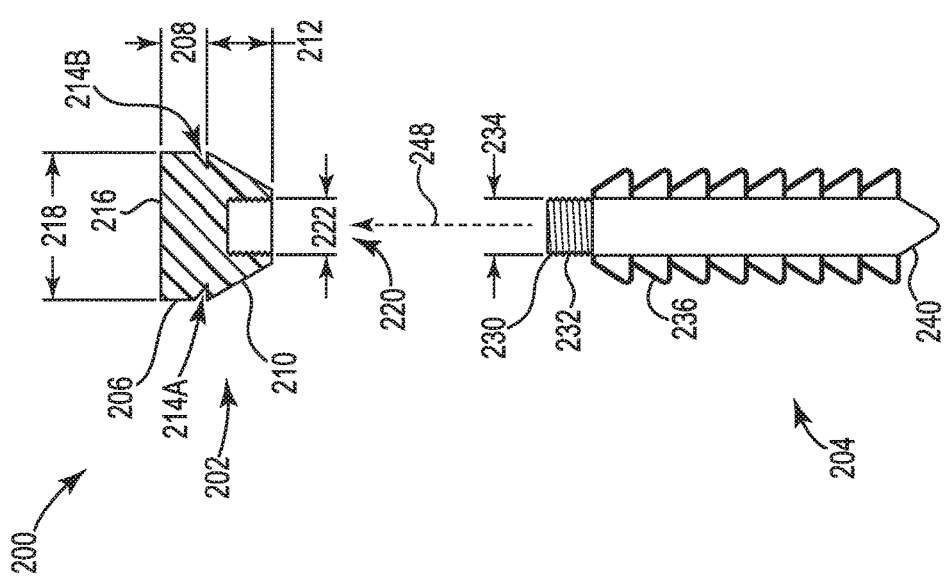

FIGS. 2A-2C illustrate disassembled and assembled cross-sectional views of an embodiment of the drive assembly 102 illustrated in FIG. 1. FIG. 2A illustrates a disassembled cross-sectional view of a drive assembly at 200 that includes a cap 202 and a lower assembly 204. Lower assembly 204 includes inner restoration apparatus 236 and an irrigation fluid drive bullet 240. In other embodiments, lower assembly 204 does not include inner restoration apparatus 236. In the illustrated embodiment, cap 202 includes an upper portion 206 having a height 208 and a lower portion 210 having a height 212. Upper portion 206 and lower portion 210 are separated by one or more indentations or notches illustrated as 214A and 214B. Cap 202 has an upper surface 216 having a width illustrated at 218 and has a lower opening 220 having a width illustrated at 222. In the illustrated embodiment, height 208 is about 0.5 cm, height 212 is about 1.0 cm, width 218 is about 2.0 cm and width 222 is about 1.0 cm. In other embodiments, height 208, height 212, width 218 and width 222 can have other suitable dimensions.

In the illustrated embodiment, lower assembly 204 includes an upper threaded portion 232 at a proximal end 230. Upper threaded portion 232 has a width 234 and is adapted to be releasably attached to cap 202 at opening 220. This is indicated by the dash line arrow at 248. In the illustrated embodiment, opening 220 is threaded in complementary fashion to threaded portion 232 and width 234 is appropriately sized to enable a threaded attachment of lower assembly 204 to cap 202. In the illustrated embodiment, widths 222 and 234 are about 1.0 cm. In other embodiments, widths 222 and 234 can have other suitable values. In various embodiments, unscrewing cap 202 from lower assembly 206 provides for cleaning of drive bullet 240 and an interior of inner restoration apparatus 236. In other embodiments, cap 202 and lower assembly 204 can be attached using other suitable approaches.

FIG. 2B illustrates an assembled cross-sectional view of a drive assembly at 250. Cap 202 includes a top surface 216. Inner restoration apparatus 236 is formed from a non-porous and elastically deformable material. In the illustrated embodiment, inner restoration apparatus 236 is adapted to store a restoration energy. In other embodiments, inner restoration apparatus 236 does not store a restoration energy. In the illustrated embodiment, inner restoration apparatus 236 has a distance or height illustrated at 238 that represents inner restoration apparatus 236 in a relaxed state before a force 266 has been applied to drive assembly 250 to store a restoration energy. Inner restoration apparatus 236 has a width illustrated at 242. Drive bullet 240 has a tip 252 that extends through distal end 254 of inner restoration apparatus 236 by a distance illustrated at 244. In the illustrated embodiment, height 238 is about 5.25 cm, width 242 is about 1.75 cm, and distance 244 is about 0.75 cm. In other embodiments, height 238, width 242 and distance 244 can have other suitable values.

FIG. 2C illustrates a cross-sectional view of drive assembly at 260 that is storing a restoration energy. Drive bullet 240 has a tip 252 that extends through distal end 254 of inner restoration apparatus 236 by a distance illustrated at 264. In the illustrated embodiment, the amount of movement of drive bullet 240 corresponds to a difference between height 238 illustrated in FIG. 2B and height 262 illustrated in FIG. 2C. In one embodiment, the distance that drive bullet 240 moves into evacuation tube 404 corresponds to a difference between distance 264 illustrated in FIG. 2C and distance 244 illustrated in FIG. 2B (see also, FIG. 9B).

Figure 3C:
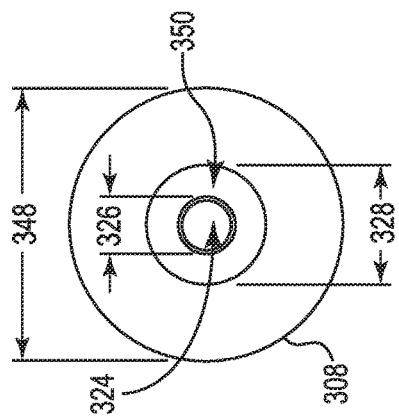
FIG. 3A-3C illustrate cross-sectional, top and bottom views of an embodiment of an evacuation chamber.
Figure 3B:
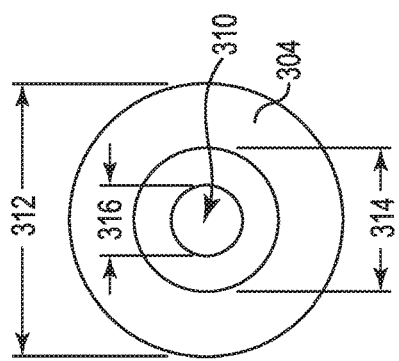
Figure 3A:
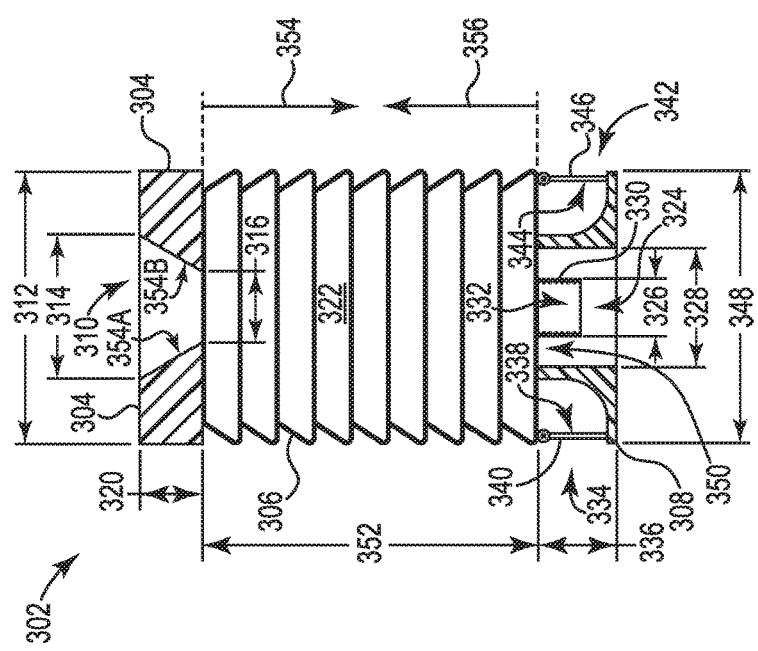

FIG. 3A-3C illustrate cross-sectional, top and bottom views of an embodiment of an evacuation chamber. FIG. 3A illustrates at 300 a cross-sectional view of an evacuation chamber 302. Evacuation chamber 302 includes an upper apparatus 304, an outer restoration chamber 306 and a lower apparatus 308. Evacuation chamber 302 includes an input port 310, an evacuation port 324 that is adapted to be in fluid communication with evacuation tube 404, and includes a vacuum port 350 that is adapted to be in fluid communication with vacuum tube 422 (see also, FIG. 4A). In the illustrated embodiment, outer restoration chamber 306 is attached to and in a fluid sealing relationship with upper apparatus 304 and with lower apparatus 308. Outer restoration chamber 306 is formed from a non-porous and elastically deformable material that defines a volume within evacuation chamber 302. In the illustrated embodiment, outer restoration chamber 306 is adapted to store a restoration energy. In other embodiments, outer restoration chamber 306 does not store a restoration energy.

FIG. 3B illustrates a top view of evacuation chamber 302. Referring to FIG. 3A and FIG. 3B, upper apparatus 304 has a width 312 and includes an input port 310. Input port 310 includes angled surfaces 354A and 354B that form a fluid sealing relationship with lower portion 210 of cap 202 when drive assembly 250 is inserted into evacuation chamber 302 (see also, FIG. 7). Input port 310 has a width 314 and a height 320. In the illustrated embodiment, width 314 and a height 320 correspond with, respectively, width 218 and height 212 of cap 202. In the illustrated embodiment, width 312 is about 4.5 cm, width 314 is about 2.0 cm, width 316 is about 1.0 cm and height 320 is about 1.0 cm. In other embodiments, width 312, width 314, width 316 and height 320 can have other suitable values. In the illustrated embodiment, input port 310 serves as an entrance point for drive assembly 250 when drive assembly 250 is inserted into evacuation chamber 302 (see also, FIG. 7). Width 316 of input port 310 is sufficiently large relative to width 242 of inner restoration apparatus 250 to enable drive assembly 250 to be inserted within evacuation chamber 302.

FIG. 3C illustrates a bottom view of evacuation chamber 302. Referring to FIG. 3A and FIG. 3C, lower apparatus 308 has an overall width 348 and a height 336. Lower apparatus 308 includes evacuation port 324 and vacuum port 350. Evacuation port 334 includes a threaded portion at 330. Evacuation port 324 is coaxial to and lies within vacuum port 350. Evacuation port 324 has a width illustrated at 326 and vacuum port 350 has a width illustrated at 328. A distance between input port 310 and evacuation port 324 is illustrated at 352. Evacuation port 326 secures and stabilizes drive assembly 250 and allows drive bullet 240 to move through evacuation port 324 upon application of a downward force 266 to drive assembly 250 that causes distance 362 to be reduced (see also, FIG. 2C). Lower apparatus 308 includes peripheral duck valves 334 and 342 that provide unidirectional air flow out and away from evacuation chamber 302. In the illustrated embodiment, valve 334 includes a valve port cover 340 and valve 342 includes a valve port cover 346. Valve port covers 340 and 346 are hingeably attached at an upper end. In the illustrated embodiment, two valves are illustrated. In other embodiments, one valve may be used or more than two valves may be used. In other embodiments, other suitable designs or implementations may be used for valves 334 and 342.

Figure 4A:
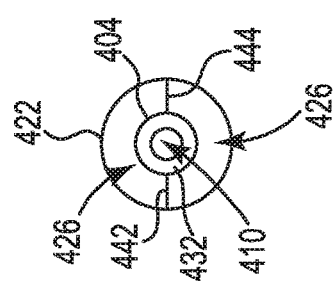
FIG. 4A-4C illustrate side, top and bottom views of an embodiment of a delivery apparatus.
Figure 4B:
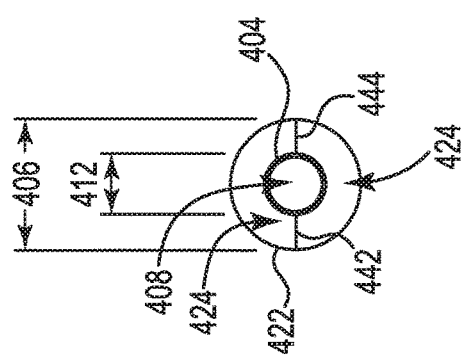
Figure 4C:
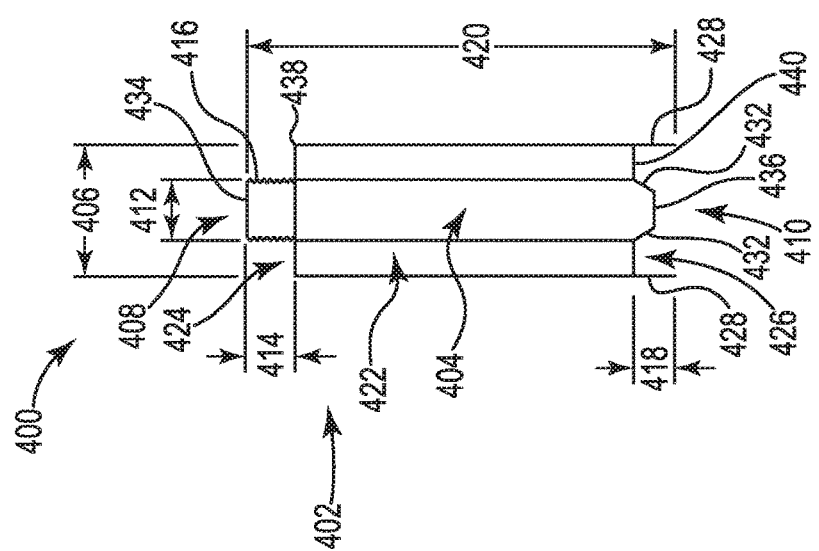

FIG. 4A-4C illustrate side, top and bottom views of an embodiment of a delivery apparatus. FIG. 4A illustrates at 400 a delivery apparatus 402. Delivery apparatus 402 includes an evacuation tube 404 that is configured to hold an irrigation solution and a vacuum tube 422 that is adapted to be in fluid communication with the evacuation chamber 302. In one embodiment, the irrigation solution is a saline solution. In other embodiments, evacuation tube 404 is configured to hold other suitable solutions. In the illustrated embodiment, a proximal end 434 of evacuation tube 404 has an input port 408 and is adapted to be attached to and in a fluid sealing relationship with evacuation port 324 of evacuation chamber 302. Evacuation tube 404 includes an output port at 410. Threaded portion 416 of evacuation tube 404 has a width 412 and is threaded and adapted to be screwed into and form a fluid sealing relationship with threaded portion 330 of lower apparatus 308 (see also, FIG. 3A). Width 412 and width 326 of evacuation chamber 302 are suitably dimensioned to enable a threaded and fluid sealing relationship between threaded portion 416 and threaded portion 330. Vacuum tube 422 includes an output port 424 and an input port 426. Width 406 and width 328 of evacuation chamber 302 are suitably dimensioned to enable a fluid sealing relationship between proximal end 438 of vacuum tube 422 and vacuum port 350 of evacuation chamber 302. Vacuum port 426 includes a lower edge 428 that is adapted to engage and form a fluid sealing relationship with a nozzle 502 or a nozzle 602 (see also, FIG. 5A and FIG. 6A). Evacuation tube 404 includes a tapered portion 432 that is also adapted to engage and form a fluid sealing relationship with a nozzle 502 or a nozzle 602.

In the illustrated embodiment, height 414 is about 0.5 cm, height 418 is about 0.5 cm and height 420 is about 6.0 cm. In other embodiments, height 414, height 418 and height 420 can have other suitable dimensions. In the illustrated embodiment, evacuation tube 404 has a volume that is within a range of 3.9 cm³ to 4.8 cm³. In other embodiments, the volume of evacuation tube 404 can have other suitable values or ranges of values. In the illustrated embodiment, evacuation tube 404 and vacuum tube 422 are formed as a single unit. In other embodiments, evacuation tube 404 and vacuum tube 422 can be formed as separate units and combined to form delivery apparatus 402.

FIG. 4B illustrates a top view of delivery apparatus 402 and FIG. 4C illustrates a bottom view of delivery apparatus 402. Evacuation tube 404 is disposed within and in a coaxial relationship with vacuum tube 422. Bridges 442 and 444 secure evacuation tube 404 to vacuum tube 422. In other embodiments, other suitable approaches can be used to retain evacuation tube 404 within vacuum tube 422.

FIGS. 5A-5C illustrate a cross-sectional, bottom and assembled view of an embodiment of a nozzle. FIG. 5A illustrates at 500 a cross-sectional view of nozzle 502 and FIG. 5B illustrates a bottom view of nozzle 502. Referring to FIG. 5A and FIG. 5B, port 506 of nozzle 502 is attached to and in a fluid sealing relationship with output port 410 at distal end 436 of evacuation tube 404. Port 508 of nozzle 502 is attached to and in a fluid sealing relationship with vacuum port 426 at distal end 440 of vacuum tube 422. Nozzle 502 includes an upper rim 504. Upper rim 504 is adapted to be retained by and form a fluid sealing relationship with lower edge 428 of vacuum tube 422. In one embodiment, upper rim 504 fits within an interior side of lower edge 428. In another embodiment, upper rim 504 fits over an exterior side of lower edge 428. In the illustrated embodiment, nozzle 502 includes a tapered portion 510 that is adapted to engage and form a fluid sealing relationship with tapered portion 432 of evacuation tube 404.

In the illustrated embodiment, nozzle 502 has a port 512 which includes a delivery port 514 and a vacuum port 516. Vacuum port 516 is exterior to and concentric with delivery port 514. In other embodiments, vacuum port 516 and delivery port 514 can have other suitable arrangements. In the illustrated embodiment, vacuum port 516 is configured to engage a human body orifice or nasal passage and provide a pathway for an aspiration fluid into vacuum tube 422. In the illustrated embodiment, nozzle 502 is configured to pass an irrigation solution from distal end 436 of evacuation tube 404 through delivery port 514 and provide a laminar flow of the irrigation solution out of delivery port 414.

FIG. 5C illustrates a cross-sectional view of a nozzle 502 that is attached to a delivery apparatus 402. Dash arrows 518 illustrate a direction of irrigation solution flow and solid arrows 520 illustrate a direction of aspiration fluid flow. Drive assembly 250 forces the irrigation solution out of distal end 436 of evacuation tube 404 and into port 506 of nozzle 502. The irrigation fluid flow continues within nozzle 502 as illustrated by arrows 518 and flows out through delivery port 514. The stored restoration energy within one or both of inner restoration apparatus 236 and outer restoration apparatus 306 creates a negative pressure within evacuation chamber 302 that operates to draw in the aspiration fluid into vacuum port 516 as illustrated by arrows 520. The aspiration fluid flows out of port 508 of nozzle 502 and continues through vacuum port 426 and into vacuum tube 422. The aspiration fluid flow continues through vacuum tube 422 and into evacuation chamber 304.

Figure 6A:
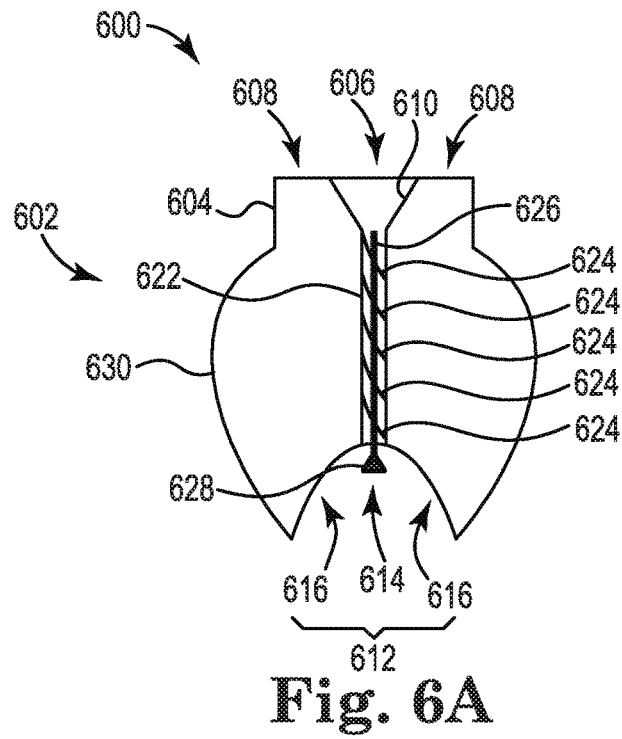
FIGS. 6A-6B illustrate cross-sectional and bottom views of an embodiment of a nozzle.
Figure 6B:
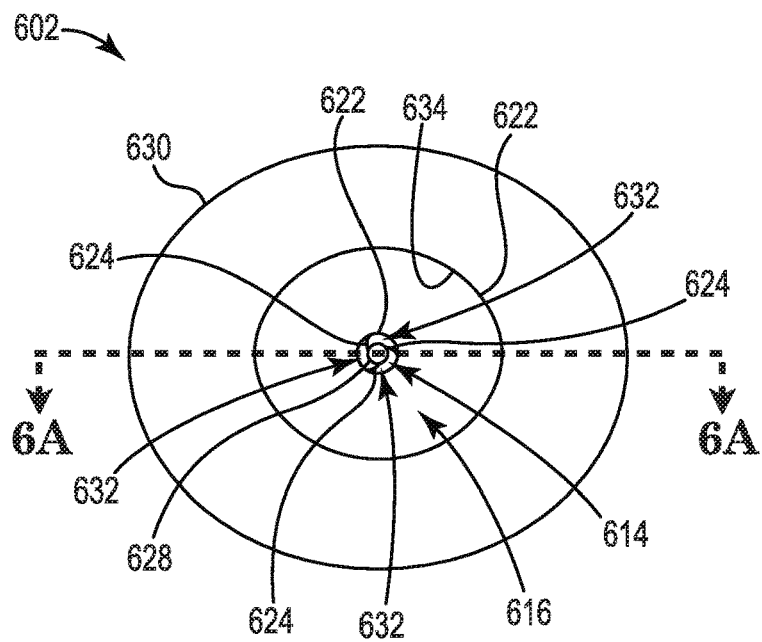

FIGS. 6A-6B illustrate a cross-sectional and bottom views of an embodiment of a nozzle. FIG. 6A illustrates at 600 a cross-sectional view of nozzle 602 and FIG. 6B illustrates a bottom view of nozzle 602. Referring to FIG. 6A and FIG. 6B, port 606 of nozzle 602 is attached to and in a fluid sealing relationship with output port 410 at distal end 436 of evacuation tube 404. Port 608 of nozzle 602 is attached to and in a fluid sealing relationship with vacuum port 426 at distal end 440 of vacuum tube 422. Nozzle 602 includes an upper rim 604. Upper rim 604 is adapted to be retained by and form a fluid sealing relationship with lower edge 428 of vacuum tube 422. In one embodiment, upper rim 604 fits within an interior side of lower edge 428. In another embodiment, upper rim 604 fits over an exterior side of lower edge 428. In the illustrated embodiment, nozzle 602 includes a tapered portion 610 that is adapted to engage and form a fluid sealing relationship with tapered portion 432 of evacuation tube 404.

In the illustrated embodiment, nozzle 602 has a port 612 which includes a delivery port 614 and a vacuum port 616.

Vacuum port 616 is exterior to and concentric with delivery port 614. In other embodiments, vacuum port 616 and delivery port 614 can have other suitable arrangements. In one embodiment, vacuum port 616 is configured to engage a human body orifice or nasal passage and provide a pathway for an aspiration fluid into vacuum tube 422. In the illustrated embodiment, nozzle 602 is configured to pass the irrigation solution between distal end 436 of evacuation tube 404 and delivery port 614.

In the illustrated embodiment, interior conduit 622 of nozzle 602 is configured to divide the irrigation solution into three circular channels 632 to increase a velocity of and provide a circular and laminar flow of the irrigation solution out of delivery port 614. In one embodiment, the three circular channels 632 operate to decrease an area of irrigation fluid flow through interior channel 622 in order to increase a speed of the irrigation fluid flow out of delivery port 614. In other embodiments, interior channel 622 is configured to divide the irrigation solution into two channels 632 or four or more channels 632. In the illustrated embodiment, interior conduit 622 includes channel dividers 624. Each channel 632 is between two adjacent channel dividers 624. Channel dividers 624 are each attached between an interior wall 634 of interior conduit 622 and a center element 626 to separate adjacent channels 632. Flow dispersion element 628 operates to increase a dispersion area of the irrigation fluid out of delivery port 614.

Figure 7:
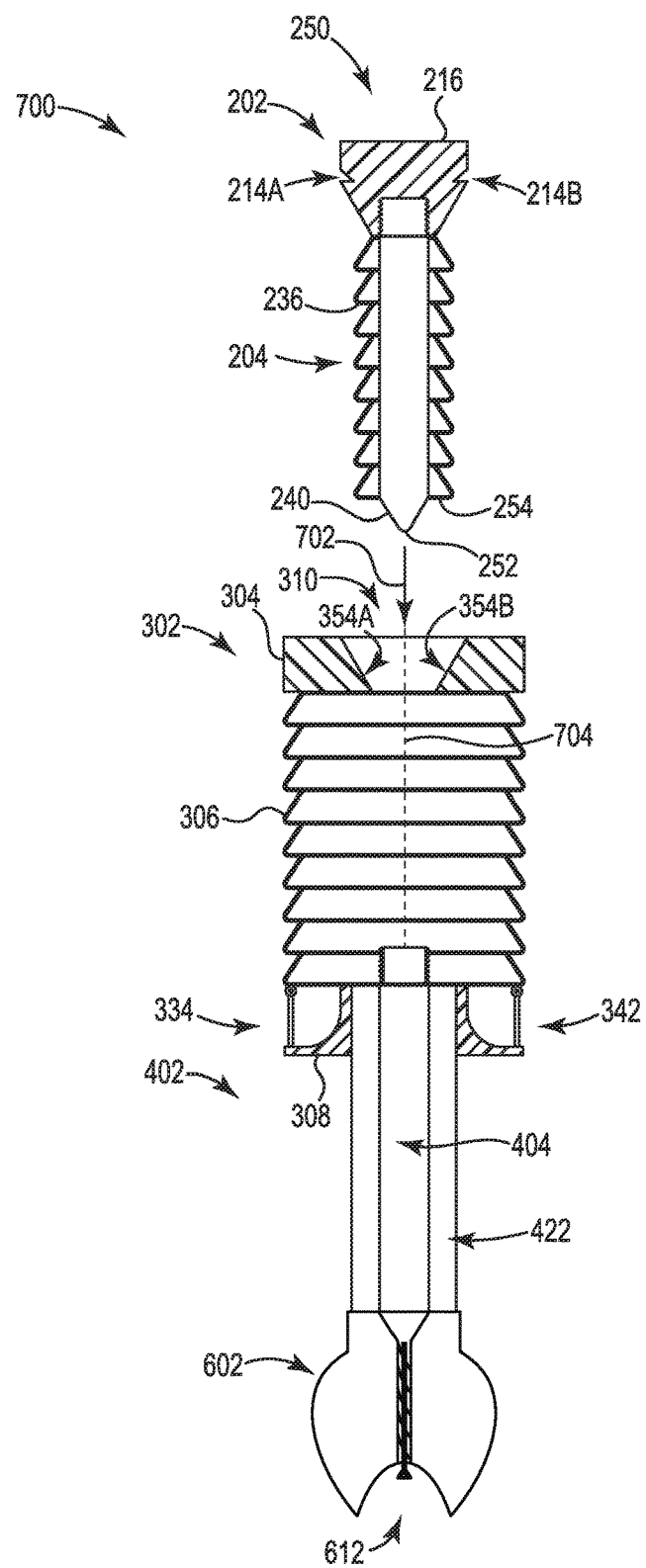
FIG. 7 illustrates a cross-sectional view of an embodiment of insertion of a drive assembly into an evacuation chamber.

FIG. 7 illustrates a cross-sectional view of an embodiment of insertion of a drive assembly 250 into an evacuation chamber 302 of an irrigation and aspiration device at 700. Drive assembly 250 is removable from evacuation chamber 302 for cleaning. Drive assembly 250 can be reinserted into input port 310 in a direction illustrated at 702. Direction 702 is in axial alignment with input port 310 and evacuation port 324 of evacuation chamber 302. This axial alignment is illustrated at 704. Once inserted, angled surfaces 354A and 354B of input port 310 form a fluid sealing relationship with lower portion 210 of cap 202 of drive assembly 250. Furthermore, evacuation port 326 of evacuation chamber 302 secures and stabilizes drive assembly 250 and allows drive bullet 240 to be moved through evacuation port 324.

FIGS. 8A and 8B illustrate a cross-sectional view of an embodiment at 800 of insertion of an irrigation fluid packet 812 into a delivery apparatus 402. Delivery apparatus 402 has a threaded portion 416 that engages or can be screwed into threaded portion 330 of evacuation chamber 302. As illustrated in FIG. 8B, delivery apparatus 402 is unscrewed from evacuation chamber 302 and an irrigation fluid packet 812 is inserted through input port 408 into evacuation chamber 404 of delivery apparatus 402. As illustrated in FIG. 8A, after insertion of irrigation fluid packet 812, delivery apparatus 402 is screwed into evacuation chamber 302 and is ready for use.

Figure 9A:
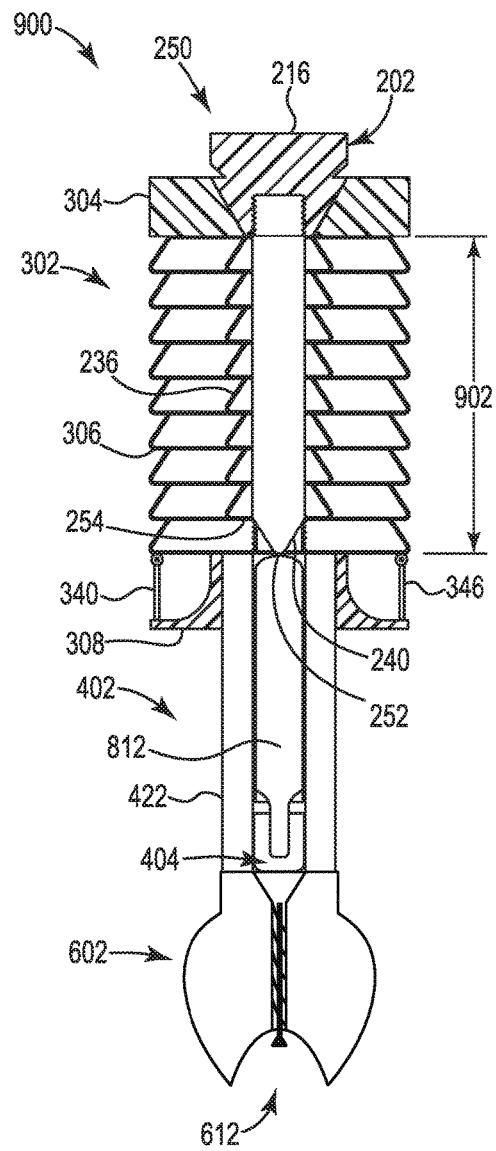
FIG. 9A-9C illustrates cross-sectional views of embodiments of using an irrigation and aspiration device.
Figure 9B:
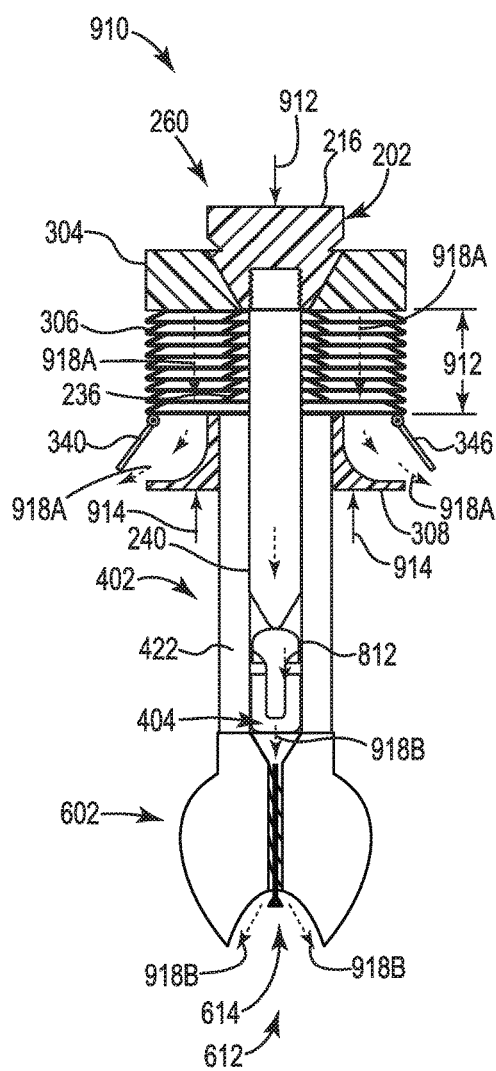
Figure 9C:
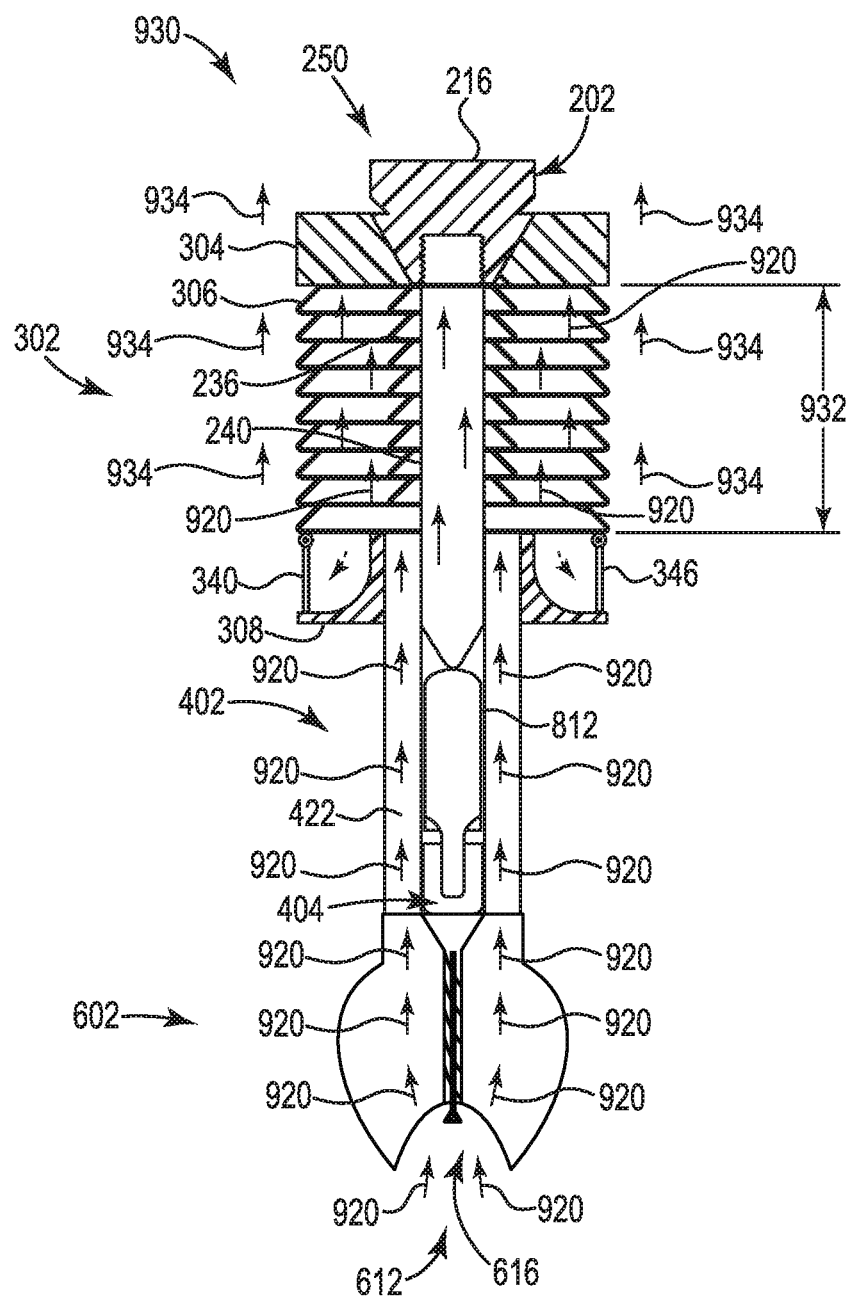

FIG. 9A-9C illustrates cross-sectional views of embodiments of using an irrigation and aspiration device. FIG. 9A illustrates an embodiment of an irrigation and aspiration device at 900 that is at equilibrium and not storing a restoration energy. A distance between input port 310 and evacuation port 324 is illustrated at 902. Distance 902 corresponds with distance 352 of outer restoration apparatus 306 as illustrated in FIG. 3A, and corresponds with distance 238 of inner restoration apparatus 236 as illustrated in FIG. 2B. In one embodiment, the restoration energy is stored within outer restoration apparatus 306 of evacuation chamber 302. In one embodiment, the restoration energy is stored within inner restoration apparatus 236 of drive assembly 250. In other embodiments, the restoration energy is stored within outer restoration apparatus 306 and at least a portion of the restoration energy is stored within inner restoration apparatus 236. In some embodiments, drive assembly 250 does not include inner restoration apparatus 236.

In the illustrated embodiment, inner restoration apparatus 236 and outer restoration apparatus 306 are formed from elastically deformable materials that store a restoration energy in response to an applied force. The stored restoration energy is a potential energy that operates to return inner restoration apparatus 236 and outer restoration apparatus 306 to their original shape once the applied force is removed. In various embodiments, the stored restoration energy corresponds to properties of the materials used to form inner restoration apparatus 236 and outer restoration apparatus 306. Device 900, which includes drive assembly 250, evacuation chamber 302, delivery apparatus 402 and nozzle 602, can be formed using any suitable material or combination of materials. These materials include, but are not limited to, materials that include rubber or plastic. FIG. 9A corresponds to inner restoration apparatus 236 and outer restoration apparatus 306 in their equilibrium or relaxed state.

In one embodiment, the stored restoration energy corresponds to Hooke's Law which is $F=KX$. For outer restoration apparatus 306 of evacuation chamber 310, F can be defined as the force applied to drive assembly 250 in the direction illustrated at 912 to store the restoration energy within outer restoration apparatus 306. Spring constant K1 can be defined as a measure of resistance or stiffness of outer restoration apparatus 306 in response to the applied force F, and X can be defined as a difference between distance 902 and distance 912 which represents the possible deformation distance of outer restoration apparatus 306.

For inner restoration apparatus 236, F can be defined as the force applied to drive assembly 250 in the direction illustrated at 912 to store the restoration energy within inner restoration apparatus 236. Spring constant K2 can be defined as a measure of resistance or stiffness of inner restoration apparatus 236 in response to the applied force F, and X can be defined as a difference between distance 902 and distance 912 which represents the possible deformation distance of inner restoration apparatus 236. The difference between distance 902 and distance 912 corresponds with the difference between distance 238 and distance 262 as illustrated in FIG. 2B and FIG. 2C, respectively. The force exerted by inner restoration apparatus 236 and/or outer restoration apparatus 306 is a restoring force and acts to restore inner restoration apparatus 236 and/or outer restoration apparatus 306 to an equilibrium state or non-compressed state. In various embodiments, K1 is greater than K2, K1 is equal to K2 or K1 is less than K2. In other embodiments, K1 is approximately equal to zero or K2 is approximately equal to zero.

FIG. 9B illustrates an embodiment of an irrigation and aspiration device at 910 when a force 912 is being applied to reduce distance 902 to distance 912. In other embodiments, distance 902 is reduced by applying a force at 914, or by applying a force at both 912 and 914. In one embodiment, device 900/910 is operated using a thumb, index and middle finger from a single hand. In this embodiment, the thumb is used to apply a force at 912, the index finger is used to apply a force at 914 (e.g., at lower apparatus 308 and proximate to valve 334 having valve port cover 340), and the middle finger is used to apply a force at 914 (e.g., at lower apparatus 308 and proximate to valve 342 having valve port cover 346).

In the illustrated embodiment drive assembly 260 is retained within the input port 310 and movably disposed within evacuation port 324 of evacuation chamber 302 and operates to, in response to the applied force 912, to simultaneously reduce the volume of the evacuation chamber 302 to store the restoration energy and move drive bullet 240 into a proximal end 434 of evacuation tube 404 to force the irrigation fluid out of distal end 436 of evacuation tube 436. In the illustrated embodiment, drive assembly 250 is moved in cooperation with evacuation chamber 302 to reduce distance 902 to distance 912 to store the restoration energy and to push tip 252 of drive assembly 250 through a proximal end 434 of evacuation tube 404 to force an irrigation fluid out of port 612 of nozzle 602 as illustrated by arrows 918B. Tip 252 of drive assembly 250 operates to create a positive fluid pressure within evacuation tube 404 to force the irrigation fluid out of distal end 436 of evacuation tube 404 as illustrated by arrow 918B, through interior conduit 622 of nozzle 602 and out of delivery port 614. Valves 334 and 342 and corresponding valve port covers 340 and 346 are in an open position when distance 902 is reduced to distance 912 which results in a volume of evacuation chamber 302 being reduced. Maintaining valves 340 and 346 in an open position when the volume of evacuation chamber 302 is reduced enables air trapped inside of evacuation chamber 302 to be released in the direction illustrated by arrows 918A in order to maintain a neutral air pressure within evacuation chamber 302.

FIG. 9C illustrates an embodiment of an irrigation and aspiration device at 930 in a state wherein a restoring force is operating to increase distance 912 to distance 902 to restore outer restoration apparatus 306 and inner restoration apparatus 236 to their equilibrium state. Distance 932 has a value that is between distance 912 and distance 902 and illustrates a device 930 that is releasing restoration energy to increase distance 932 as measured between input port 310 and evacuation port 350. In the illustrated embodiment, evacuation port 324 and is proximate to vacuum port 350, and distances 902, 912 and 932 have a same value whether measured between input port 310 and evacuation port 324 or between input port 310 and vacuum port 350. Releasing the restoration energy to increase distance 932 creates a negative pressure within evacuation chamber 302 that operates to draw an aspiration fluid into vacuum port 616 of nozzle 602. Maintaining valves 334 and 342 in a closed position when the volume of evacuation chamber 302 is increased results in the negative air pressure within evacuation chamber 302 drawing in the aspiration fluid through vacuum port 350. The aspiration fluid flow is illustrated by arrows 920. The aspiration fluid is drawn in through port 608 of nozzle 602 and through vacuum port 426 of vacuum tube 422. The aspiration fluid flow continues through vacuum port 350 and into evacuation chamber 302.

Figure 10:
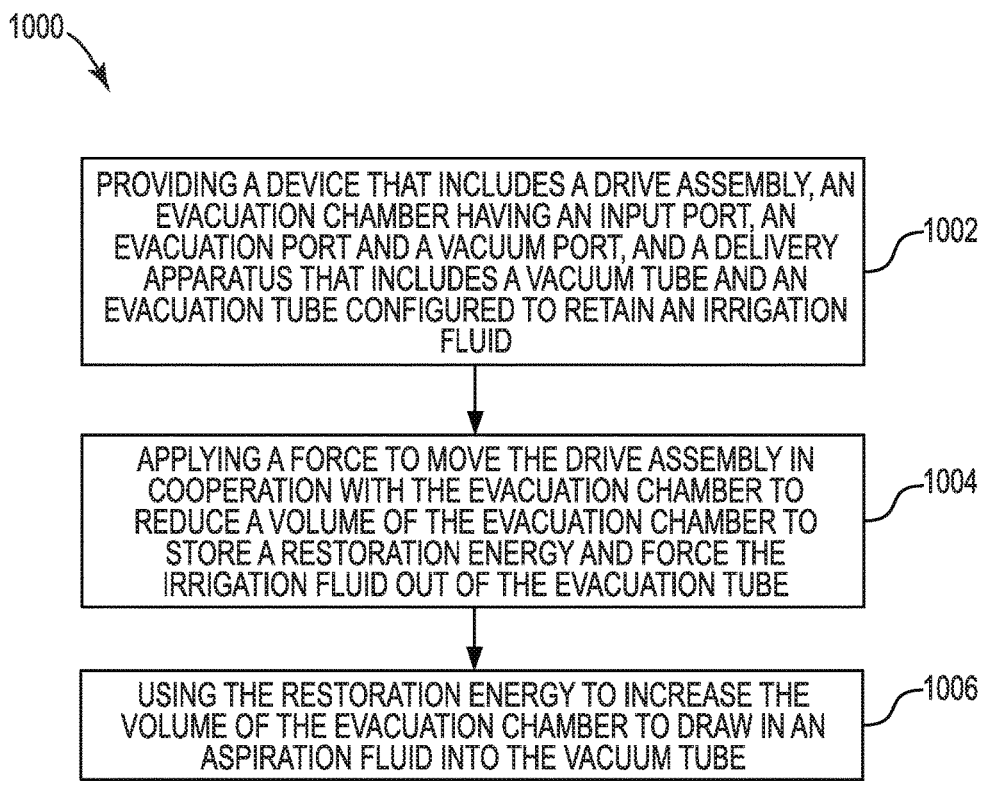
FIG. 10 illustrates a flowchart of an embodiment of a method of using an irrigation and aspiration device.

FIG. 10 illustrates a flowchart of an embodiment of a method of using an irrigation and aspiration device. The method is illustrated at 1000. At 1002, a device 100 is provided that includes a drive assembly 250, an evacuation chamber 302 having an input port 310, an evacuation port 324 and a vacuum port 350, and a delivery apparatus 402 that includes a vacuum tube 422 and an evacuation tube 404 configured to retain an irrigation fluid.

At 1004, a force is applied to move drive assembly 250 in cooperation with evacuation chamber 302 to reduce a volume of evacuation chamber 302 to store a restoration energy and force the irrigation fluid out of evacuation tube 302. In one embodiment, moving drive assembly 250 in cooperation with evacuation chamber 302 to reduce a volume of evacuation chamber 302 includes moving drive assembly 250 in a direction 912 that is axial to input port 310 and evacuation port 324 to reduce distance 912 between input port 310 and the evacuation port 324. In one embodiment, reducing a volume of evacuation chamber 302 includes opening valves 334 and 342 to maintain a neutral pressure within evacuation chamber 302. In one embodiment, forcing the irrigation fluid out of evacuation tube 404 includes dividing the irrigation solution into two or more circular channels to increase a velocity of and provide a circular and laminar flow of the irrigation solution out of evacuation tube 404.

At 1006, the restoration energy is used to increase the volume of evacuation chamber 302 to draw in an aspiration fluid into vacuum tube 422. In one embodiment, increasing the volume of evacuation chamber 302 includes closing valves 334 and 342 to maintain a negative pressure within evacuation chamber 302. In one embodiment, using the restoration energy to increase the volume of evacuation chamber 302 includes using the restoration energy stored within evacuation chamber 302 to increase the distance 352 between input port 310 and evacuation port 324. In one embodiment, using the restoration energy to increase the volume of evacuation chamber 302 includes using the restoration energy stored within drive assembly 250 to increase the distance 352 between input port 310 and evacuation port 324.

Spatially relative terms such as "under", "below", "lower", "over", "upper" and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc. and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

With the above range of variations and applications in mind, it should be understood that the present invention is not limited by the foregoing description, nor is it limited by the accompanying drawings. Instead, the present invention is limited only by the following claims and their legal equivalents.

What is claimed is:

1. An irrigation and aspiration device, comprising:
   an evacuation chamber that defines an interior volume and includes a unidirectional valve port and a vacuum port, wherein the unidirectional valve port opens in a direction that is transverse to a longitudinal axis of the evacuation chamber and provides unidirectional air flow out of and away from the evacuation chamber in a direction that is radial to the longitudinal axis when the interior volume of the evacuation chamber is reduced, and wherein the vacuum port opens in a direction of the longitudinal axis and draws an aspiration fluid through the vacuum port and into the evacuation chamber in the direction of the longitudinal axis when the interior volume of the evacuation chamber is increased;
   a delivery apparatus that includes an evacuation tube and a vacuum tube, wherein the evacuation tube has a proximal end and a distal end and is configured to hold an irrigation solution between the proximal end and the distal end, and wherein the vacuum tube has a proximal end attached to the vacuum port and is in fluid communication with the evacuation chamber; and a drive assembly configured to store a restoration energy while reducing the interior volume of the evacuation chamber to push a tip of the drive assembly through the proximal end of the evacuation tube to force the irrigation solution out of the distal end of the evacuation tube while simultaneously forcing air inside the interior volume of the evacuation chamber out through the unidirectional valve port, in response to an applied force, and use the restoration energy to increase the interior volume of the evacuation chamber to draw the aspiration fluid into a distal end of the vacuum tube and through the vacuum tube and the vacuum port into the interior volume of the evacuation chamber.

2. The device of claim 1, wherein the evacuation chamber comprises a non-porous and elastically deformable chamber that includes an input port.

3. The device of claim 2, wherein the drive assembly is retained within the input port and movably disposed within the evacuation port.

4. The device of claim 3, wherein the drive assembly includes a restoration apparatus, and wherein the drive assembly is configured to store at least a portion of the restoration energy within the restoration apparatus.

5. The device of claim 3, wherein the evacuation chamber is configured, in response to the restoration energy, to increase the interior volume to create a negative pressure that is configured to draw in the aspiration fluid through the distal end of the vacuum tube.

6. The device of claim 5, wherein the unidirectional valve port is configured to be in an open position when the interior volume is reduced and in a closed position when the interior volume is increased.

7. The device of claim 3, wherein the delivery apparatus comprises a nozzle that includes a delivery port and is attached to and in a fluid sealing relationship with the distal end of the evacuation tube, and wherein the nozzle is configured to divide the irrigation solution between the distal end of the evacuation tube and the delivery port into two or more circular channels to increase a velocity of and provide a circular and laminar flow of the irrigation solution out of the delivery port.

8. An irrigation and aspiration device, comprising:

an evacuation chamber that defines an interior volume and includes an input port, an evacuation port, a vacuum port and a unidirectional valve port, wherein the unidirectional valve port opens in a direction that is transverse to a longitudinal axis of the evacuation chamber and provides unidirectional air flow out of and away from the evacuation chamber in a direction that is radial to the longitudinal axis when the interior volume of the evacuation chamber is reduced, and wherein the vacuum port opens in a direction of the longitudinal axis and draws an aspiration fluid through the vacuum port and into the evacuation chamber in the direction of the longitudinal axis when the interior volume of the evacuation chamber is increased;

a drive assembly in axial alignment with the input port and the evacuation port, wherein the input port and the evacuation port are separated by a distance, and wherein the drive assembly is configured to be releasably retained within the input port and movably engaged within the evacuation port;

a delivery apparatus that includes an evacuation tube and a vacuum tube, wherein the evacuation tube has a proximal end and a distal end and is configured to retain an irrigation fluid between the proximal end and the distal end, wherein the proximal end of the evacuation tube is attached to and in a fluid sealing relationship with the evacuation port and a proximal end of the vacuum tube is attached to and in a fluid sealing relationship with the vacuum port, wherein the drive assembly is configured to be moved in cooperation with the evacuation chamber to reduce the distance between the input port and the evacuation port to store a restoration energy and reduce the interior volume of the evacuation chamber to force air inside the evacuation chamber out through the unidirectional valve port while simultaneously pushing a distal end of the drive assembly into the proximal end of the evacuation tube to force the irrigation fluid out of the distal end of the evacuation tube, and wherein releasing the restoration energy increases the distance between the input port and the evacuation port to increase the interior volume of the evacuation chamber and create a negative pressure within the evacuation chamber that is configured to draw in the aspiration fluid from a distal end of the vacuum tube and through the vacuum tube and the vacuum port into the interior volume of the evacuation chamber.

9. The device of claim 8, wherein the unidirectional valve port is configured to be in an open position when the distance between the input port and the evacuation port is reduced and in a closed position when the distance between the input port and the evacuation port is increased.

10. The device of claim 8, wherein the evacuation tube is disposed within and in a coaxial relationship with the vacuum tube.

11. The device of claim 10, wherein the delivery apparatus comprises a nozzle attached to and in a fluid sealing relationship with the distal end of the evacuation tube and the distal end of the vacuum tube, wherein the nozzle includes a delivery port and is configured to divide the irrigation solution between the distal end of the evacuation tube and the delivery port into two or more circular channels to increase a velocity of and provide a circular and laminar flow of the irrigation solution out of the delivery port, wherein the nozzle includes a vacuum port that is exterior to and concentric with the delivery port, and wherein the vacuum port is configured to engage a human body orifice and provide a pathway for the aspiration fluid between the vacuum port and the distal end of the vacuum tube.

12. The device of claim 8, wherein the drive assembly includes a restoration apparatus, and wherein the drive assembly is configured to store at least a portion of the restoration energy within the restoration apparatus.

13. A method of irrigating and aspirating a nasal cavity, comprising:

providing a device that includes a drive assembly, an evacuation chamber defining an interior volume and having an input port, an evacuation port, a vacuum port and a unidirectional valve port, wherein the unidirectional valve port opens in a direction that is transverse to a longitudinal axis of the evacuation chamber and provides unidirectional air flow out of and away from the evacuation chamber in a direction that is radial to the longitudinal axis when the interior volume of the evacuation chamber is reduced, and wherein the vacuum port opens in a direction of the longitudinal axis and draws an aspiration fluid through the vacuum port and into the evacuation chamber in the direction of the longitudinal axis when the interior volume of the evacuation chamber is increased, and wherein the device includes a delivery apparatus that includes a vacuum tube and an evacuation tube configured to retain an irrigation fluid between a proximal end and a distal end of the evacuation tube;

applying a force to move the drive assembly in cooperation with the evacuation chamber to reduce the interior volume of the evacuation chamber to store a restoration energy and force air inside the interior volume of the evacuation chamber out through the unidirectional valve port while simultaneously pushing a tip of the drive assembly through the proximal end of the evacuation tube to force the irrigation fluid out of the distal end of the evacuation tube, and using the restoration energy to increase the interior volume of the evacuation chamber to draw in the aspiration fluid into a distal end of the vacuum tube and through the vacuum tube and the vacuum port into the interior volume of the evacuation chamber.

14. The method of claim 13, wherein moving the drive assembly in cooperation with the evacuation chamber to reduce the interior volume of the evacuation chamber comprises moving the drive assembly in a direction that is axial to the input port and the evacuation port to reduce a distance between the input port and the evacuation port.

15. The method of claim 14, wherein using the restoration energy to increase the interior volume of the evacuation chamber comprises enabling the restoration energy stored within the evacuation chamber to increase the distance between the input port and the evacuation port.

16. The method of claim 14, wherein using the restoration energy to increase the interior volume of the evacuation chamber comprises enabling the restoration energy stored within the drive assembly to increase the distance between the input port and the evacuation port.

17. The method of claim 13, wherein reducing the interior volume of the evacuation chamber comprises opening the unidirectional valve port to maintain a neutral pressure within the evacuation chamber, and wherein increasing the interior volume of the evacuation chamber comprises closing the unidirectional valve port to maintain a negative pressure within the evacuation chamber.

18. The method of claim 13, wherein forcing the irrigation fluid out of the evacuation tube comprises dividing the irrigation solution into two or more circular channels to increase a velocity of and provide a circular and laminar flow of the irrigation solution out of the evacuation tube.

* * * * *